United States Patent [19]

Heinrich

[11] Patent Number: 4,777,170

[45] Date of Patent: Oct. 11, 1988

[54] METHOD TO PREVENT AND TREAT THE SIGNS AND SYMPTOMS OF MOTION SICKNESS

[76] Inventor: William A. Heinrich, 565 Ashland Rd., Middlesex, N.J. 08846

[21] Appl. No.: 10,551

[22] Filed: Feb. 3, 1987

[51] Int. Cl.[4] .............................. A61U 31/54
[52] U.S. Cl. .................................. 514/226.2
[58] Field of Search ........................ 514/223

Primary Examiner—Stanley J. Friedman

[57] ABSTRACT

Motion sickness is a disorder thought to be caused by the excessive stimulation of the vestibular apparatus caused by angular and linear acceleration and deceleration sometimes resulting in nausea and vomiting. Characteristic signs and symptoms of the condition in addition to nausea and vomiting include yawning, hyperventilation, salivation, pallor, profuse cold sweating, somnolence, aerophagia, dizziness, headache, general discomfort, fatigue, weakness, and inability to concentrate. When prolonged motion sickness is accompanied by vomiting, hypotension, dehydration, inanition and depression may occur. The present invention includes methods for prevention of motion sickness as well as methods for the treatment of the signs and symptoms of motion sickness after their onset.

10 Claims, No Drawings

METHOD TO PREVENT AND TREAT THE SIGNS AND SYMPTOMS OF MOTION SICKNESS

BACKGROUND OF THE INVENTION

The present invention relates to the prevention of motion sickness and to the treatment of the signs and symptoms of motion sickness in warm-blooded animals and particularly in humans.

The condition known as motion sickness has commonly been thought to caused chiefly by sea, air, car, train, and space travel as well as carnival-type amusements, and other types of motion. A variety of drugs have been used to prevent and treat motion sickness: specifically these include phenothiazines (i.e., chlorpromazine, perphenazine, prochlorperazine, promethazine, triethylperazine, triflupromazine), antihistamines (i.e., cyclizine, dimenhydrinate, diphenhydramine, meclizine, hydroxyzine, buclizine), anticholinergics (i.e., scopolamine), sedatives (i.e., phenobarbital, pentobarbital), benzodiazepines (i.e., diazepam), benzquinamide, diphenidol, trimethobenzamide, bismuth subsalicylate, fructose and glucose.

Promethazine Hydrochloride, or as known chemically as N,N,α-trimethyl-10H-phenothiazine-10-ethanamine monohydrochloride, has the structural formula

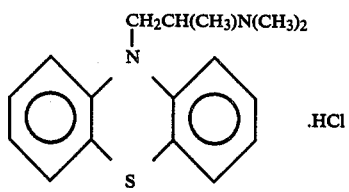

is a known staple of commerce used in the treatment of nausea and vomiting and as an expectorant, antihistamine, and sedative, when taken in combination with pseudoephedrine hydrochloride, or as known chemically as (1-methylamino)-ethyl benzyl alcohol HCl, has the structural formula

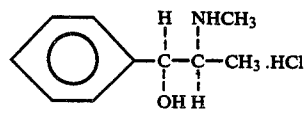

is a known staple of commerce used in the treatment of acute coryza, eustacian tube congestion, vasomotor rhinitis, and aerotitis media and as an adjunct to analgesics, antihistamines, antibiotics, antitussives, or expectorants for optimum results in allergic rhinitis, croup, acute and subacute sinusitis, acute otitis media, and acute tracheobronchitis, acts to prevent motion sickness if consumed prior to development of the motion sickness and acts to alleviate the signs and symptoms commonly associated with motion sickness if consumed after the development of the motion sickness. It was founded that in individuals who frequently developed motion sickness that when promethazine hydrochloride was consumed with pseudoephedrine hydrochloride the development of the signs and symptoms of motion sickness was prevented in more instances than the use of promethazine hydrochloride or the use of pseudoephedrine hydrochloride alone. It was also founded that in individuals who had developed the signs and symptoms of motion sickness that when promethazine hydrochloride was consumed with pseudoephedrine hydrochloride the signs and symptoms were alleviated in more instances than the use of promethazine hydrochloride or the use of pseudoephedrine hydrochloride alone.

SUMMARY OF THE INVENTION

A combination of two agents for the prevention of or the treatment of the signs and symptoms of motion sickness in warm-blooded animals and particularly in humans, the agents being of the phenothiazine family such as promethazine hydrochloride and of the sympathiminetics family such as pseudoephedrine hydrochloride in addition with any suitable agents such as, but not limited to, tablets, capsules, liquids, suppositories, injections, transdermal patches, ophthalmic preparations, solutions, ointments, creams and gels.

The combination of formulation is that consisting of 10 mg. to 100 mg. of promethazine hydrochloride and 10 mg. to 150 mg. of pseudoephedrine hydrochloride. These amounts have been arrived at through experimentation with various proportions of the respective agents and have been found to be the most useful in terms of safety and efficacy of the combination. The preferred formulation for an adult was found to be 25 mg. of promethazine hydrochloride and 60 mg. of pseudoephedrine hydrochloride administered three times daily or approximately every six hours; this corresponds closely with the dosage and regimen commonly used for each agent independently.

PHARMACEUTICAL PRESENTATION

The compositions according to my invention are conveniently in a form suitable for oral, rectal, parenteral or topical administration in suitable pharmaceutical vehicles. Tablets may be prepared as follows but not limited to the mixing of 25 mg. of promethazine hydrochloride and 60 mg. of pseudoephedrine hydrochloride with the required amounts of lactose, microcrystalline cellulose, corn starch, talc, stearic acid and magnesium stearate and compressed into tablets. The resultant tablet may be sugar coated or film coated to mask taste or enteric coated to dissolve in the intestine instead of the stomach.

Capsules may be prepared as follows but not limited to the mixing of 25 mg. of promethazine hydrochloride and 60 mg. of pseudoephedrine hydrochloride with the required amount of lactose, microcrystalline cellulose, corn starch, talc, stearic acid and magnesium stearate and encased in a casing of gelatin, glycogelatin, or another suitable material. The nature of this material is chosen in relation to the point in the digestive system at which it is desired to release the enclosed contents.

Syrups, liquids, and elixirs may be prepared as follows but not limited to the dissolving or suspending of 25 mg. of promethazine hydrochloride and 60 mg. of pseudoephedrine hydrochloride in an aqueous liquid media which may contain preservatives such as methylparaben, propylparaben, or sodium citrate, sweetening agents such as sugar, saccharin, glycerol or sorbitol, flavoring agents such as alcohol, citrate, or artificial flavor. In the case of a suspension, surface-active agents such as glyceryl monostearate, aluminum monostearate, hydroxycellulose or hydroxymethyl cellulose may be incorporated to maintain the suspension. The thixotropy and viscosity of the liquid medium of the syrup, suspension, elixir, or liquid may be adjusted by inclusion of appropriate amounts of pectin, gelatin, gum tragacanth, carboxymethyl cellulose or agar-agar. Colorants may also be incorporated.

Injectable preparations may be prepared by forming solutions and/or suspensions in any of the usual sterile media. Preferably these preparations are rendered isotonic with the body fluids and rendered pyrogen-free during preparation.

Creams for application to the skin may be formulated by the mixing of an aqueous phase, such as water, with a fat phase, such as petrolatum, and incorporation of an emulsifier, such as cholesterol. Ointments may be formulated with petrolatum or polyethylene glycol admixtures. Lotions may be formulated by the addition of an aqueous phase, such as water, to a fat phase, such as mineral oil, with the addition of glycerol monostearate, polyethylene 100 stearate, lanolin alcohol, methylparaben, propylparaben and glycerin. The cream, ointment, and lotion formulations additionally contain as their active components promethazine hydrochloride and pseudoephedrine hydrochloride and when applied topically to the skin the active components promethazine hydrochloride and pseudoephedrine hydrochloride pass through the skin and enter into the blood and/or lymph systems.

Suppositories may be formulated by addition of promethazine hydrochloride and pseudoephedrine hydrochloride to a cocoa butter base and molded into suppository form.

Transdermal patches may be formulated by addition of promethazine hydrochloride and pseudoephedrine hydrochloride to a suitable silicone base and curing the base. Said patch may be attached to the skin allowing the promethazine hydrochloride and pseudoephedrrine hydrochloride to pass through the skin and enter into the blood and/or lymph systems.

Therefore, be it understood that it is the purpose of this invention to inform that any means of delivery known in the art and science of pharmacy can be employed to deliver the promethazine hydrochloride and pseudoephedrine hydrochloride into the body of human or animal to prevent or treat the signs and symptoms of motion sickness. This and other purposes will now be further illustrated by the following examples:

EXAMPLE 1

A male, 37 years of age, had previously experienced motion sickness each time he would go fishing on a boat for the past 20 years. He was treated with 25 mg. of promethazine hydrochloride and 60 mg. of pseudoephedrine hydrochloride three hours prior to a boat fishing trip. He did not experience any signs and symptoms of motion sickness on the trip, despite the 17 foot boat rocking for 8 hours in 3-4 foot seas in the Atlantic Ocean. It should be noted that a followup dose was administered 6 hours after the first.

EXAMPLE 2

The same male as noted in example 1 was subject to another boat fishing trip two weeks after the above mentioned trip. He was not medicated before the trip. After only 20 minutes of rocking in the same 17 foot boat in seas of 3-4 feet, he became nauseated and began to vomit. A liquid form of 25 mg. promethazine hydrochloride and 60 mg. pseudoephedrine hydrochloride was administered while he was still in the boat and in approximately 20 minutes the nausea and vomiting had dissipated.

EXAMPLE 3

The same male as in example 1 partook of another boat fishing experience the following week and was given 25 mg. of promethazine hydrochloride 1 hour prior to launch. While he did not experience any nausea and vomiting in the 4 foot swells, he did become sleepy and lethargic, disinterested in the fishing.

EXAMPLE 4

The same male as in example 1 on a subsequent weekend went on another boat fishing trip in the same 17 foot boat and was premedicated with 60 mg. of pseudoephedrine hydrochloride alone 2 hours before departure. After one-half hour of rocking in the two foot swells, the subject began to vomit, but recovered quickly. After approximately another half hour had elapsed, the subject vomited again, after which he was administered 25 mg. of promethazine hydrochloride in liquid form. No nausea and/or vomiting was seen for the rest of the trip, which was 2 hours.

EXAMPLE 5

A 28 year old female with a history of motion sickness accompanying air travel was administered 25 mg. of promethazine hydrochloride and 60 mg. of pseudoephedrine hydrochloride 2 hours prior to departure of a 4-hour flight. The woman experienced no symptoms of nausea or vomiting during the flight despite moderate to heavy turbulence in the air.

EXAMPLE 6

A nine year old male child who experienced chronic motion sickness in an automobile was administered 12.5 mg. of promethazine hydrochloride and 30 mg. of pseudoephedrine hydrochloride in liquid form one hour prior to leaving on a car trip. Despite the varied driving conditions encountered on the 2 hour trip, no signs of symptoms of nausea or vomiting were percieved by the child or his parents.

EXAMPLE 7

A 42 year old female who had chronically experienced nausea, but only occasional vomiting, while taking a daily mass-transit train on a 45-minute trip each way was given 25 mg. of promethazine hydrochloride and 60 mg. of pseudoephedrine hydrochloride one hour prior to departure each way for one week. No signs or symptoms of nausea or vomiting were experienced during that time.

EXAMPLE 8

A 33 year old male who had complained of not being able to deep-sea fish because of his inability to keep from vomiting either from the rocking of the boat or the intense diesel exhaust fumes was subjected to just that on a 65 foot fishing boat after being pre-medicated with 25 mg. of promethazine hydrochloride and 60 mg. of pseudoephedrine hydrochloride one hour prior to leaving. The man experienced no signs or symptoms of nausea or vomiting during the entire 5 hour trip.

EXAMPLE 9

A 26 year old female had complained that during her glider pilot instruction, the erratic movement of the craft had caused her to become nauseous and uncomfortable. Prior to a trip (1 hour) she was given 25 mg. of promethazine hydrochloride and 60 mg. of pseudoephedrine hydrochloride in tablet form. She experienced none of the symptoms of which she had previously complained.

EXAMPLE 10

A 24 year old male had embarked on a fishing trip on a 65 foot boat. Three hours into the trip, the individual began to vomit as the swells were approaching 8 feet. He was administered 25 mg. of promethazine hydrochloride alone and while the vomiting ceased within 30 minutes of his taking the second dose (the first dose was eliminated by vomiting within 10 minutes of its administration and the second dose was immediately given), the subject fell asleep and was awakened two hours later near the trip's completion.

I have found that the use of promethazine hydrochloride in combination with pseudoephedrine hydrochloride at doses of 12.5–25 mg. of promethazine hydrochloride and 30–60 mg. of pseudoephedrine hydrochloride depending on the subject administered one to three hours prior to the development of the signs and symptoms of motion sickness will prevent the development of the signs and symptoms of motion sickness in all cases better than the use of promethazine hydrochloride or the use of pseudoephedrine hydrochloride alone. Additionally, I have discovered that the use of promethazine hydrochloride and pseudoephedrine hydrochloride in the above noted doses caused the alleviation of the signs and symptoms of motion sickness when taken after the signs and symptoms developed, better than the use of promethazine hydrochloride or the use of pseudoephedrine hydrochloride alone.

What is claimed is:

1. A method for the prevention of motion sickness, said method comprising the administering, to a person prior to the development of the signs and symptoms of motion sickness, a combination of from 10 mg. to 100 mg. of promethazine hydrochloride and from 10 mg. to 150 mg. of pseudoephedrine hydrochloride.

2. A method for the treatment of motion sickness, said method comprising the administering, to a person exhibiting the signs and symptoms of motion sickness, a combination of from 10 mg. to 100 mg. of promethazine hydrochloride and from 10 mg. to 150 mg. of pseudoephedrine hydrochloride.

3. A method of claim 1 wherein a pharmaceutical composition containing a combination of from 10 mg. to 100 mg. of promethazine hydrochloride and from 10 mg. to 150 mg. of pseudoephedrine hydrochloride is administered to a patient.

4. A method of claim 2 wherein a pharmaceutical composition containing a combination of from 10 mg. to 100 mg. of promethazine hydrochloride and from 10 mg. to 150 mg. of pseudoephedrine hydrochloride is administered to a patient.

5. A composition for the prevention of motion sickness, said composition consisting of from 10 mg. to 100 mg. of promethazine hydrochloride and from 10 mg. to 150 mg. of pseudoephedrine hydrochloride.

6. A composition for the treatment of motion sickness, said composition consisting of a combination of from 10 mg. to 100 mg. of promethazine hydrochloride and from 10 mg. to 150 mg. of pseudoephedrine hydrochloride.

7. A method for the prevention of motion sickness, said method comprising the administering to an adult person prior to the development of the signs and symptoms of motion sickness 25 mg. of promethazine hydrochloride combined with 60 mg. of pseudoephedrine hydrochloride.

8. A method for the treatment of motion sickness, said method comprising the administering to an adult person exhibiting the signs and symptoms of motion sickness 25 mg. of promethazine hydrochloride combined with 60 mg. of pseudoephedrine hydrochloride.

9. The method of claim 7 wherein a pharmaceutical composition containing 25 mg. of promethazine hydrochloride and 60 mg. of pseudoephedrine hydrochloride is administered to a patient.

10. The method of claim 8 wherein a pharmaceutical composition containing 25 mg. of promethazine hydrochloride and 60 mg. of pseudoephedrine hydrochloride is administered to a patient.

* * * * *